United States Patent [19]

Vowinkel et al.

[11] 4,000,642
[45] Jan. 4, 1977

[54] PROCESS AND DEVICE FOR TESTING THE THERMOSTABILITY OF SHAPED ARTICLES OF THERMOPLASTIC MATERIAL

[75] Inventors: Hans Vowinkel, Florsheim, (Main); Hans Röber, Frankfurt am Main, both of Germany

[73] Assignee: Hoechst Aktiengesellschaft, Frankfurt am Main, Germany

[22] Filed: July 24, 1975

[21] Appl. No.: 598,627

[30] Foreign Application Priority Data

July 26, 1974 Germany .......................... 2435999

[52] U.S. Cl. ............................................. 73/15 R
[51] Int. Cl.² ...................................... G01N 25/00
[58] Field of Search .................... 73/15 R, 15.4, 159

[56] References Cited

UNITED STATES PATENTS

| | | | |
|---|---|---|---|
| 2,895,327 | 7/1959 | Monego et al. | 73/15 |
| 3,148,531 | 9/1964 | Stoll et al. | 73/15 |
| 3,292,418 | 12/1966 | Oehme et al. | 73/15 |
| 3,373,599 | 3/1968 | Higginbottom | 73/15 |

FOREIGN PATENTS OR APPLICATIONS 1,104,262    11/1955   France ................................. 73/15

OTHER PUBLICATIONS

Pfahl et al., "Simultaneous Measurement of Six Thermal Properties of a Charring Plastic", in J. Heat-Mass Transfer, vol. 13, No. 2, pp. 275-286, 1970.

Primary Examiner—Herbert Goldstein
Attorney, Agent, or Firm—Curtis, Morris & Safford

[57] ABSTRACT

The thermostability of shaped articles of thermoplastic material is determined by the visible alteration of the surface of the article caused by a focused hot gas jet which is blown onto the surface. The temperature of the gas and the gas rate hitting the surface per unit of time, and also the residence time of the shaped article under the influence of the hot gas jet are a measure for the thermostability.

4 Claims, 1 Drawing Figure

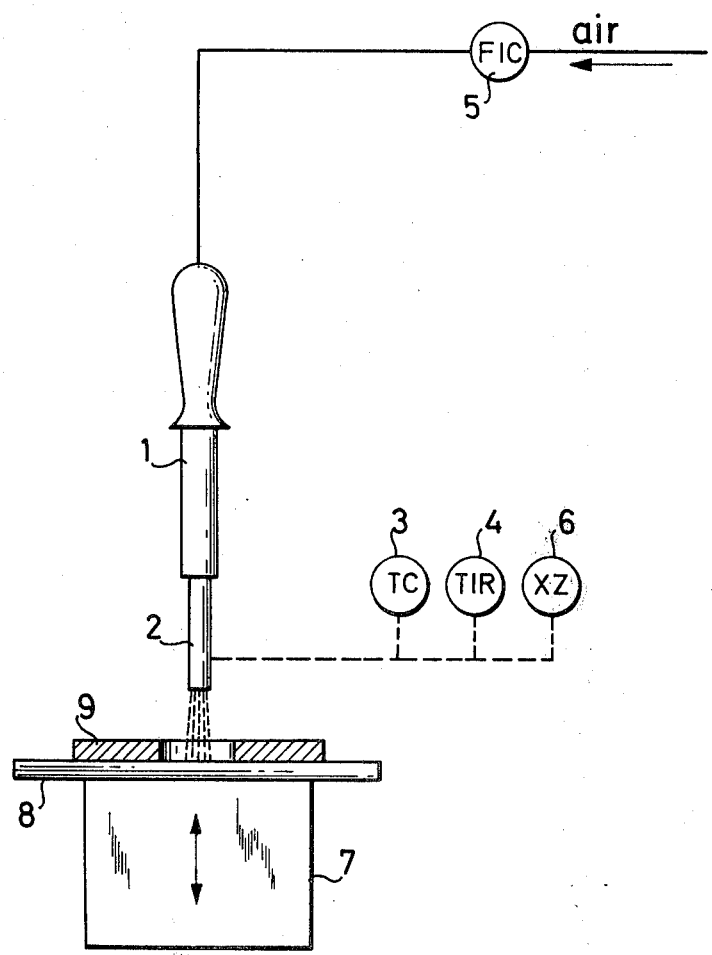

PROCESS AND DEVICE FOR TESTING THE THERMOSTABILITY OF SHAPED ARTICLES OF THERMOPLASTIC MATERIAL

The present invention provides a process and a device for testing the thermostability of thermoplastic material.

Various processes have been developed for testing the thermostability of raw material for plastics and for shaped articles as well as for the determination of thermal damage to articles of plastic material already in use (see J. Voigt, Die Stabilisierung der Kunststoffe gegen Licht und Warme, Springer Verlag 1966, p. 475 sqq.). All these processes require much expenditure and time. The results of the test hitherto carried out are generally relative to thick layer of the sample; conclusions on the stability of thin surface layers could be drawn only with difficulty. There existed therefore a demand for a test to be carried out rapidly, for example for series and routine examinations, and a process for testing the thermostability of thin surface layers.

It has now been found that the thermostability or the thermostability reserve of a shaped article of plastic material can be determined in a simple and rapid manner by using a focused jet of hot gas. At constant temperature and gas flow, the time that elapses until a clearly visible alteration of the surface hit by the jet occurs is a direct measure the stability. The transition point is very exactly detectable and reproducible, and it is generally spontaneous.

The present invention provides therefore a process for testing the thermostability of shaped articles of thermoplastic material which comprises blowing a focused jet of hot gas onto the surface of a shaped article and determining the time that elapses until the surface is visibly altered by the hot gas, the end of which time is evidenced by a transition point specific for each kind of plastic material.

The process of the invention for testing the thermostability of shaped articles of thermoplastic material may be advantageously carried out with an apparatus comprising a gas heating device with gas feeder and gas outlet for a focused jet of hot gas, and an adjustable support for the shaped article to be tested; the gas feeder being provided with equipment for controlling and measuring the gas throughput, and the gas outlet being provided with a thermocouple connected with a thermostat, a temperature recorder and plotter, and a pressure-sampling device connected with a chronometer.

The test conditions, especially temperature and throughput of the gas jet, and the distance between the surface of the sample of the gas outlet nozzle have to be adapted to the various plastic materials, that is, their stability and sensitivity to heat, in order to obtain well differentiated test results. The optimum test conditions determined individually for each plastic material are maintained constant in all of the following tests of the material in question. Preferably, a surface area of from 3 to 100 mm$^2$ is hit by the jet of gas heated to a temperature of from 200° to 500° C. It is especially recommended to deliver the jet of hot gas from a cylindrical gas outlet (nozzle) having a diameter of from 2 to 10 mm at a flow rate of from 10 to 100 l/minute. In principle, however, other nozzles, for example of conical or non-circular shape may be used. The distance from the gas nozzle to the surface to be tested amounts preferably to 5 to 50 mm.

The gas jet should hit the surface of the sample advantageously at an angle of from 45° to 90°; vertical blowing being preferred.

For economic reasons, the gas used should be preferably air. It is also possible to obtain increased oxidation by using oxygen, or to produce a purely thermal degradation by employing inert gases, for example nitrogen.

The present invention will be better understood by reference to the drawing which is a schematic representation of an embodiment of the device according to the invention for carrying out the test process.

Referring now to the drawing, the device comprises a gas heating apparatus 1 with cylindrical gas outlet 2, a thermostat 3, equipment for recording and plotting the gas temperature 4, equipment for controlling and measuring the gas throughput 5, a chronometer 6, an adjustable support 7 for holding the test sample 8 in place and for fixing the distance from the gas outlet 2 to the surface of the plastic material to be tested. If necessary, the test sample may be covered by a template 9. The thermocouple and the pressure-sampling device are not shown in the drawing. As gas heater there may be used for example normal hot gas welding equipment. In order to increase the accuracy of measurement it may be advantageous to protect the test device from draft. The purely thermal stability has to be determined in an inert atmosphere, and an inert gas has to be used as heat carrier. A special advantage of the test process according to the invention resides in the fact that after a few seconds of testing, evidence of the thermostability of the tested products is already visible. Furthermore, the test apparatus is relatively inexpensive, and the measuring device is not necessarily stationary, so that the measurements may be taken where the plastics articles are used, for example at construction sites.

For these reasons, the test process according to the invention is especially suitable for rapid routine or series tests, for example in raw material control or in the case of quality supervision of finished goods. Possible damage caused by processing or storage etc. can thus be easily detected. For this purpose, the residual thermostability of plastics articles already used or to be applied is compared with the original stability of the raw material. By measuring the stability on the surface and on a section, it is also possible to show whether the damage is only superficial, caused for example by exposure to light, or extends throughout the material, that is, caused by thermal influence during the manufacturing process.

The test process according to the invention may also be applied in product research, for it allows a rapid and efficient checking of new stabilizer formulations. The test conditions, however, have to be exactly adapted to each product. For testing polyolefins and polyvinyl chloride, a distance of from 5 to 20 mm between the surface of the test sample and the nozzle end is recommended. The gas flow should be in a range of from 20 to 50 l/minute, and the gas temperature in a range of from 250° to 350° C, measured in the center of the hot gas jet within the nozzle of the burner.

The following examples illustrate the invention.

EXAMPLE 1

Polypropylene having a density of 0.92 g/cm$^3$ and a melt index MFI 230/5 of 1.3 g/10 minutes was blended with the stabilizers indicated in the following Table, extruded to plates, and subsequently, the thermostability of the plates was tested by means of the device as shown in the drawing. The distance between the surface of the sample and the nozzle end was 10 mm, the air flow 30 l/min and the gas temperature 320° C. The end of the elapsed time at which degradation of the material occurs is defined by the moment when a liquid film on the sample spatters in the form of rays. 1 to 2 seconds before, the surface takes on a greasy brilliancy.

| Tests | A | B | C |
| --- | --- | --- | --- |
| stabilizer | weight % | weight % | weight % |
| 3,3-bis-(4-hydroxy-phenyl)-butanoic acid dodecyl ester | 0.1 | 0.5 | 0.5 |
| dioctadecyl disulfide | 0.15 | 0.15 | 0.15 |
| dilauryl-thio dipropionate | — | — | 0.35 |
| calcium stearate | 0.2 | 0.2 | 0.2 |
| zinc sulfide | — | 1.5 | 1.5 |
| elapsed time until degradation of material occurred (sec.) | 7 | 20 | 26 |

The Table shows clearly how the elapsed time until degradation of the material occurred depends on the amount and kind of stabilization.

EXAMPLE 2

From the blend according to Example 1C, bottles were manufactured by extrusion blowing. Sample D was manufactured under normal processing conditions. In the case of Sample E, the preform was exposed to air for a longer time than required; improper processing conditions were deliberately chosen. The test conditions were as indicated in Example 1. In the case of Sample D, degradation started after 26 seconds, Sample E degraded after only 7 seconds; that is, the thermostability of the bottles was severely deteriorated by the improper processing conditions, while the stability of the bottles manufactured according to the prescriptions (Sample D) was the same as that of Example 1C.

EXAMPLE 3

A wall covering element made of a mixture of 90 weight % of PVC having K value of 70, and of 10 weight % of chloropolyethylene (chlorine content 40 weight %), stabilized with 1.5 weight % of Cd/Ba laurate, 0.5 weight % of diphenylisooctyl phosphite, 2.0 weight % of oxidized soybean oil, 0.3 weight % of hydroxystearic acid and 0.1 weight % of a polyethylene wax, each relative to the polymer mixture, was tested by means of the device of the invention. The distance from the surface of the sample to the nozzle end was 10 mm, the air flow 30 l/min and the gas temperature 280° C. After a blowing time of 38 seconds, the surface treated had discolored to a slightly brown shade.

A wall covering element manufactured from the same mixture, but which was deliberately damaged thermally by improper processing conditions showed the indicated discoloration after only 28 seconds. This difference of the test results indicates the extent of degradation caused by thermal damage during the manufacturing process.

What is claimed is:
1. A process for testing the thermostability of shaped articles of thermoplastic material which comprises blowing a focused jet of hot gas at a temperature of 200° to 500° C. onto the surface of a shaped article and determining the time that elapses before the surface is visibly altered by the hot gas, said gas jet being delivered from a cylindrical nozzle having a diameter of from 2 to 10 mm. at a flow rate of 10 to 100 liters per minute.
2. A process according to claim 1 wherein said gas jet is focused on a surface area of said shaped article of from 3 to 100 mm$^2$.
3. A process according to claim 1 wherein the distance between the gas nozzle and the surface to be tested is from 5 to 50 mm.
4. A process according to claim 1 wherein the gas jet impinges on the surface to be tested to an angle of from 45° to 90°.

* * * * *